US011253289B2

(12) United States Patent
Rack

(10) Patent No.: US 11,253,289 B2
(45) Date of Patent: Feb. 22, 2022

(54) DEVICE FOR SEVERING AND REMOVING TISSUE PARTS

(71) Applicant: Morpheus AG, Spaichingen (DE)

(72) Inventor: Timo Rack, Weilheim (DE)

(73) Assignee: MORPHEUS AG, Spaichingen (DE)

( * ) Notice: Subject to any disclaimer, the term of this patent is extended or adjusted under 35 U.S.C. 154(b) by 131 days.

(21) Appl. No.: 15/746,454

(22) PCT Filed: Jul. 22, 2016

(86) PCT No.: PCT/EP2016/067497
§ 371 (c)(1),
(2) Date: Jan. 22, 2018

(87) PCT Pub. No.: WO2017/013240
PCT Pub. Date: Jan. 26, 2017

(65) Prior Publication Data
US 2018/0206877 A1 Jul. 26, 2018

(30) Foreign Application Priority Data

Jul. 23, 2015 (DE) .................... 10 2015 112 025.9
Aug. 3, 2015 (DE) .................... 10 2015 112 716.4
Aug. 28, 2015 (DE) .................... 10 2015 114 306.2

(51) Int. Cl.
*A61B 17/32* (2006.01)
*A61B 17/3205* (2006.01)
*A61B 17/16* (2006.01)

(52) U.S. Cl.
CPC .... *A61B 17/32053* (2013.01); *A61B 17/1608* (2013.01); *A61B 17/1611* (2013.01); *A61B 17/1635* (2013.01); *A61B 17/1659* (2013.01); *A61B 2017/320064* (2013.01); *A61B 2217/005* (2013.01); *A61B 2217/007* (2013.01)

(58) Field of Classification Search
CPC .......... A61B 17/32053; A61B 17/1608; A61B 17/1611
See application file for complete search history.

(56) References Cited

U.S. PATENT DOCUMENTS

| 4,522,206 | A | 6/1985 | Whipple et al. |
| 6,653,713 | B2 | 11/2003 | Takasu |
| 2005/0267503 | A1* | 12/2005 | Hunstad ............. A61B 17/1671 606/170 |
| 2006/0122615 | A1 | 6/2006 | McKinley |
| 2011/0190802 | A1* | 8/2011 | Mark ............... A61B 17/32053 606/171 |

FOREIGN PATENT DOCUMENTS

| DE | 3802907 A1 | 8/1989 |
| DE | 19513572 A1 | 10/1996 |

OTHER PUBLICATIONS

International search report for patent application No. PCT/EP2016/067497 dated Nov. 3, 2016.

* cited by examiner

*Primary Examiner* — Olivia C Chang
(74) *Attorney, Agent, or Firm* — Bachman and Lapointe PC

(57) ABSTRACT

A device for severing and removing tissue parts (20), from a body of a living being, by means of a fixed guide rail (1, 30) along which a slide rail (6, 31) is movable, wherein the guide rail (1, 30) and the slide rail (6, 31) form, in the distal region, a cutting or punching mouth (17, 32) for severing the tissue part (20), wherein a conduit (18) for supplying a liquid is assigned to the cutting or punching mouth (17).

20 Claims, 10 Drawing Sheets

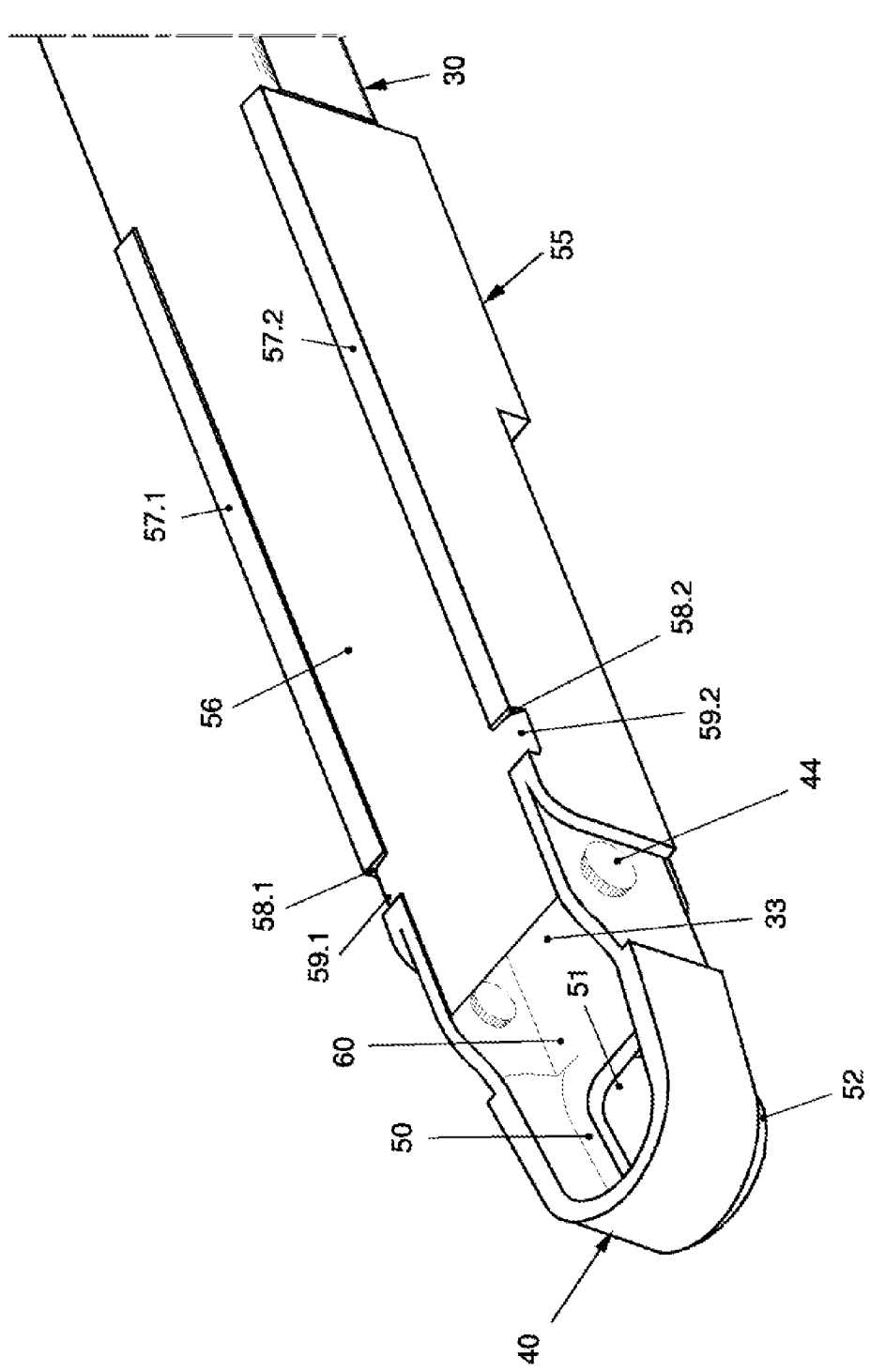

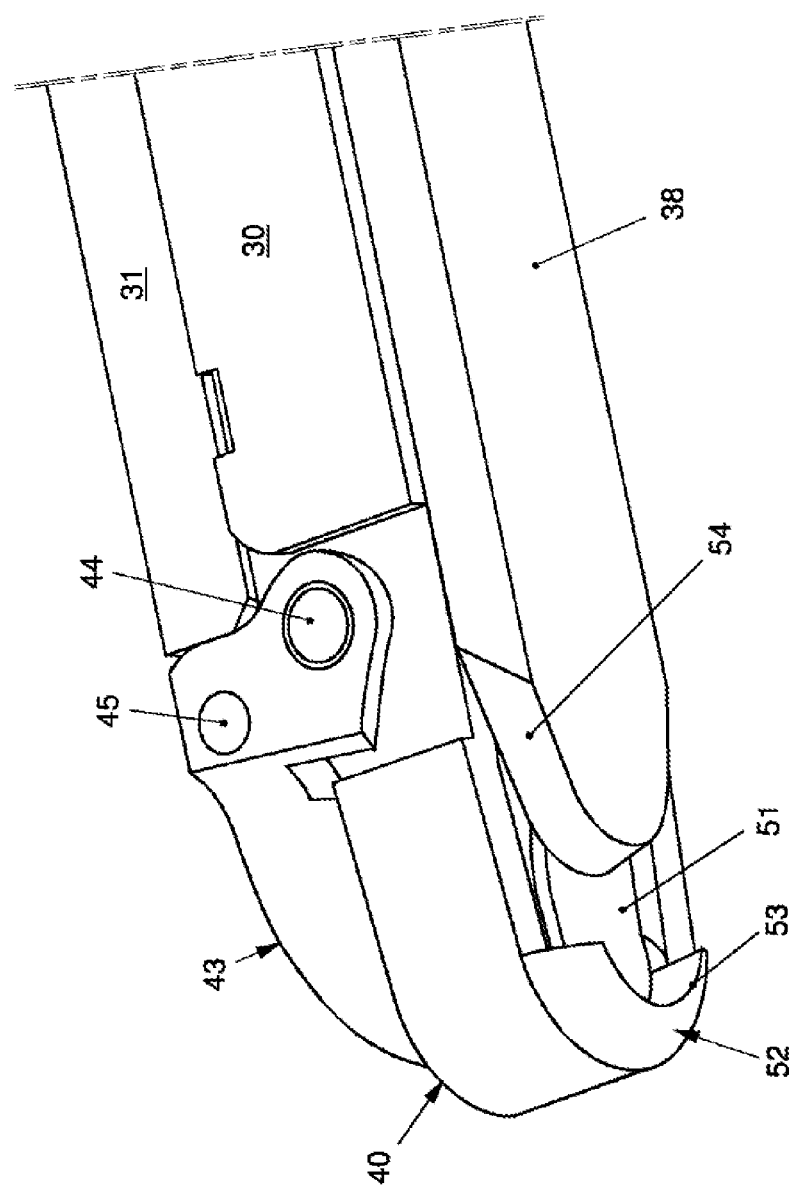

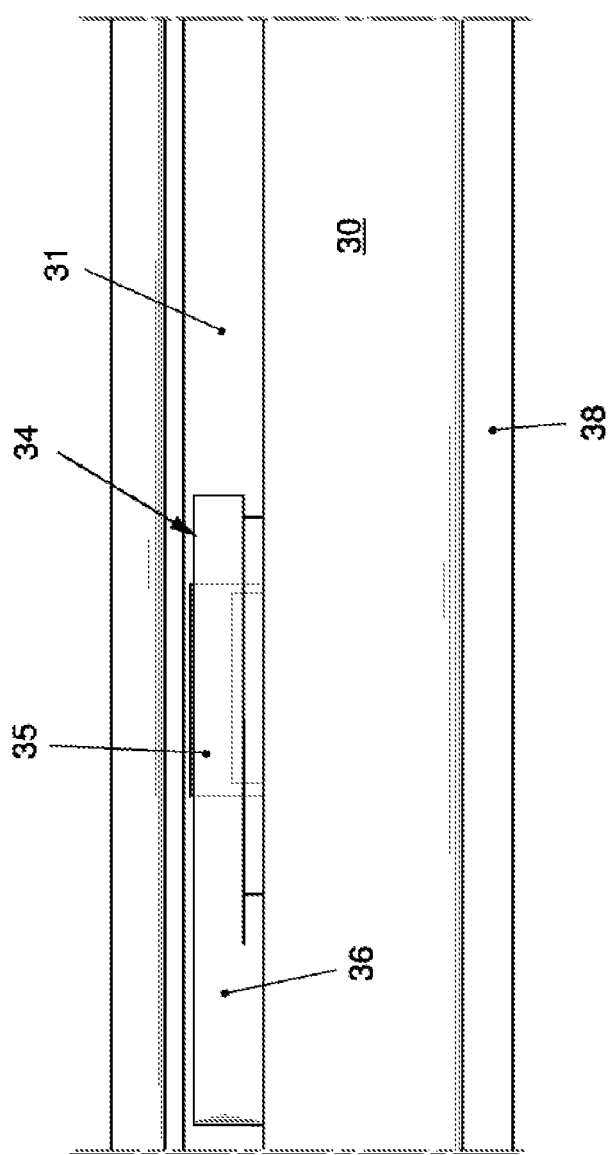

DEVICE FOR SEVERING AND REMOVING TISSUE PARTS

BACKGROUND OF THE INVENTION

The invention relates to a device for severing and removing tissue parts, in particular from a body of a living being, by means of a fixed guide rail along which a slide rail is movable, wherein the guide rail and the slide rail form, in the distal region, a cutting or punching mouth for severing the tissue part.

PRIOR ART

Medical devices with cutting forceps for collecting tissue samples or for removing elongate body elements such as nerve or vein segments or the like are known with two forceps arms that have an outer tube and an inner tube. The inner tube in most cases serves to actuate a scissor element. The tissue segment that has been cut off is then aspirated through the inner tube.

So-called tissue or bone punches are known and available on the market in many different shapes and designs. Reference is made here, merely by way of example, to DE 195 13 572 C2, which discloses a surgical instrument with a shaft and a carriage that is arranged slidably and releasably on the shaft. The carriage is connected releasably to a grip part, and the shaft is connected to a main grip part. A mating element, against which a cutting edge at the distal end of the carriage can be driven, protrudes from the distal end of the shaft. In this way, a tissue part is punched out.

US 2006/0122615 A1 and U.S. Pat. No. 5,653,713 A disclose tissue punches in which a channel is formed that serves for the aspiration of tissue parts.

SUMMARY OF THE INVENTION

The object of the present invention is to configure a known bone or tissue punch of this kind so that it is more versatile in use and provides improved suction.

The object is achieved by the fact that a conduit for supplying a liquid is assigned to the cutting and punching mouth.

This liquid not only serves to flush the operating site but is also intended to be largely aspirated together with the tissue part that is to be removed. This means that a short circuit as it were is formed between the suction channel and the outlet opening of the conduit, such that the liquid enters the suction channel immediately after leaving the conduit. This ensures that the tissue parts are flushed through the suction channel.

Tissue parts are to be understood in particular, but not exclusively, as muscle tissue, connective tissue and support tissue, including bone parts, cartilage and adipose tissue, epithelial tissue and also nerve tissue. It is intended to include any part of a living being that can be removed using a conventional tissue and/or bone punch.

In the previously known tissue and/or bone punches, the slide rail and guide rail are generally connected to each other at intervals along almost their entire length. In most cases, a sliding block protrudes from one part and is guided in a T-shaped groove in the other part. This is of course also possible in the present invention. However, it is preferable that slide rail and guide rail are coupled to each other only at the distal end. Here, any kind of guide is conceivable and is intended to be covered by the invention. In a simple illustrative embodiment, the guide rail has at the distal end, preferably on both sides, a guide groove in which a rail of the slide rail engages in each case.

In order to form an actual punch, a mating cutting element should be provided protruding at the distal end of the guide rail. It is best here if this mating cutting element is formed in one piece from the guide rail.

At its border, the mating cutting element forms a semi-circular cutting edge which interacts with a semi-oval cutting opening in the distal end of the slide rail. The cutting or punching mouth thus formed can be designed as in known punches, i.e. the semi-oval cutting opening is bounded by a cutting edge which engages bluntly on the mating cutting element. However, according to the present preferred illustrative embodiment, the mating cutting element is intended to be able to travel into the cutting opening of the cutting rail. That is to say, during the movement of the slide rail along the guide rail, the distal end of the slide rail is guided over the mating cutting element, wherein the two cutting edges interact like scissors. It is intended here that one cutting edge be set at an inclination to the other cutting edge, such that the cutting and punching mouth closes in the manner of scissors, and the cutting process is thus substantially improved.

The tissue parts are also carried off more efficiently if the cavity formed by the cutting and punching mouth opens toward the suction channel. This can also be done in steps.

In a further illustrative embodiment of the invention for which protection is also requested separately, but especially together with the conduit discussed above, the guide rail is intended to form a suction channel for removal of the severed tissue part. The functionality of the previously known tissue or bone punches is thereby substantially enhanced. It means that this kind of instrument can now also be used without additional effort being needed for aspiration of tissue parts. The slide rail simply has to be configured as a suction channel. It is conceivable here that the suction channel is integrated in the slide rail, i.e. that the slide rail itself is hollow. It is of course also conceivable that the slide rail together with the guide rail forms a relatively closed suction channel or that the slide rail alone forms a suction channel. These concepts are also intended to be covered by the present invention. For each of these, protection is requested separately, but especially together with the conduit.

The suction channel begins with the cutting or punching mouth, or with a collecting space for tissue parts that is formed by this mouth. It merges at the other end into a connector nipple, for example for a suction hose, such that the tissue part can then be collected in a container for example. A valve is also preferably connected upstream to this connector nipple, with which valve it is possible to also shut off the suction channel such that the device can be used quite generally as a cutting or bone punch.

The slide rail is intended to be connected to the guide rail. The guide rail is generally designed to be fixed, and the slide rail is intended to be displaceable along this fixed guide rail. How the connection is made is of secondary consideration. It is conceivable, for example, for sliding blocks on one rail to be guided in corresponding grooves of the other rail. If the device is also intended to be easily releasable or dismantlable, then these connections are configured accordingly. There are sufficient examples for this in the prior art.

An essential element of the present invention is the configuration of the cutting or punching mouth. It is conceivable that a part of this cutting or punching mouth is designed to be fixed. In this case, this part can be formed integrally from the guide rail, for example. However, it is also conceivable for it to be arranged on a push-on element which is connected, preferably releasably, to the guide rail. The releasability ensures that the fixed part can be replaced by any other part, including also by a movable part, without extensive changes having to be made to the entire device.

The fixed part can now be assigned a movable cutting element, which is connected preferably in an articulated manner to the slide rail. In a preferred illustrative embodiment, this cutting element is spoon-shaped and interacts with the fixed part in order to permit cutting. Both elements form respective cutting edges which interact in order to sever a tissue part. Within the context of the invention, part of the cutting edges is also concave, preferably extending concavely on both sides toward a tip. This has the advantage that, particularly if the tip is arranged on the movable cutting element, said tip can be made to dig into the tissue and draws the tissue part to be severed toward it or into the collecting space of the cutting or punching mouth. The concave configuration of the cutting edge then has the additional advantage that there is only a scissors-like, punctiform severing of the tissue part, such that the force that has to be applied can be kept low.

In a further illustrative embodiment of the invention, liquid is intended to be able to be supplied to the cutting or punching mouth. The liquid can be water, for example. This is done via a conduit which opens out near the cutting or punching mouth. To ensure that the liquid can also pass into the interior of the cutting or punching mouth, the cutting element is intended to have a corresponding recess.

In a particular illustrative embodiment of the invention, for which protection is also requested separately, the device is used as a curette, that is to say as a scraper device. In this case, a corresponding scraper element is provided at the tip, or at the distal end of the guide rail, which scraper element has a relatively sharp cutting or scraping edge. To ensure that a scraped-off tissue part can be carried away, the fixed part of the cutting or punching mouth additionally has, in its bottom near the scraper element, an opening through which the scraped-off tissue part can enter the collecting space of the cutting or punching element. It is then aspirated through the abovementioned suction channel.

If the scraper element is not used, i.e. if the device is not used as a curette, then the aforementioned opening in the fixed part of the cutting or punching mouth should also be able to be closed. For this purpose, a corresponding closure slide or closure strip is provided under the guide rail and can be operated from the direction of a grip part of the device. For example, an additional trigger slide can be provided for this purpose near the forceps grips of the device, which trigger slide is able to slide along the guide rail and moves the closure slide.

BRIEF DESCRIPTION OF THE DRAWINGS

Further advantages, features and details of the invention will become clear from the following description of preferred illustrative embodiments and by reference to the drawing, in which:

FIG. 8 shows an enlarged perspective plan view of a part of the distal end of the device from FIG. 5;

FIG. 9 shows an enlarged perspective bottom view of the distal end of the device from FIG. 5;

FIG. 10 shows an enlarged transparent detail, in a side view, of the device from FIG. 5.

DETAILED DESCRIPTION

Figure 1:
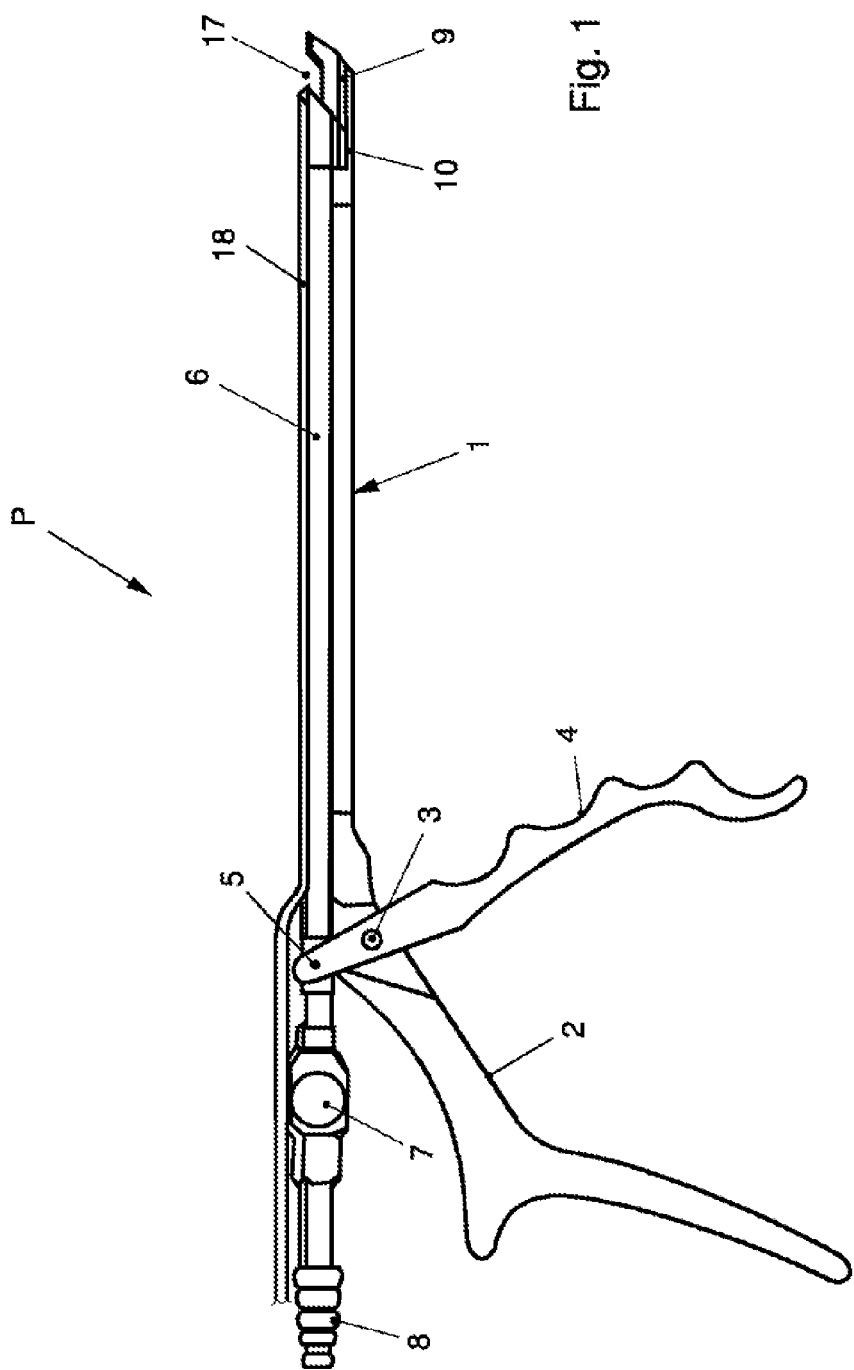
FIG. 1 shows a plan view of a device according to the invention for severing and removing tissue parts, with an opened cutting or punching mouth.

A device P according to the invention for severing and removing tissue parts 20, in particular from a body of a living being, is designed similarly to a known tissue punch. The device P has a guide rail 1 which, in this illustrative embodiment, merges integrally into a forceps grip 2. A further forceps grip 4 is connected to the forceps grip 2 via a rotary joint 3 and forms an articulated connection 5 with a slide rail 6. After the articulated connection 5, the slide rail 6 opens into a rotary valve 7, which transitions into a connector nipple 8, for example for attachment of a suction hose. A movement of the slide rail 6 with respect to the guide rail 1 is effected by a closing movement of the two forceps grips 2 and 4 relative to each other, wherein the slide rail 6 is connected at the distal end of the device P to the guide rail 1. For this purpose, guide grooves 9 are formed on both sides in the guide rail 1, in each of which guide grooves 9 an inwardly directed rail 10 of the slide rail 6 is guided.

Figure 4:
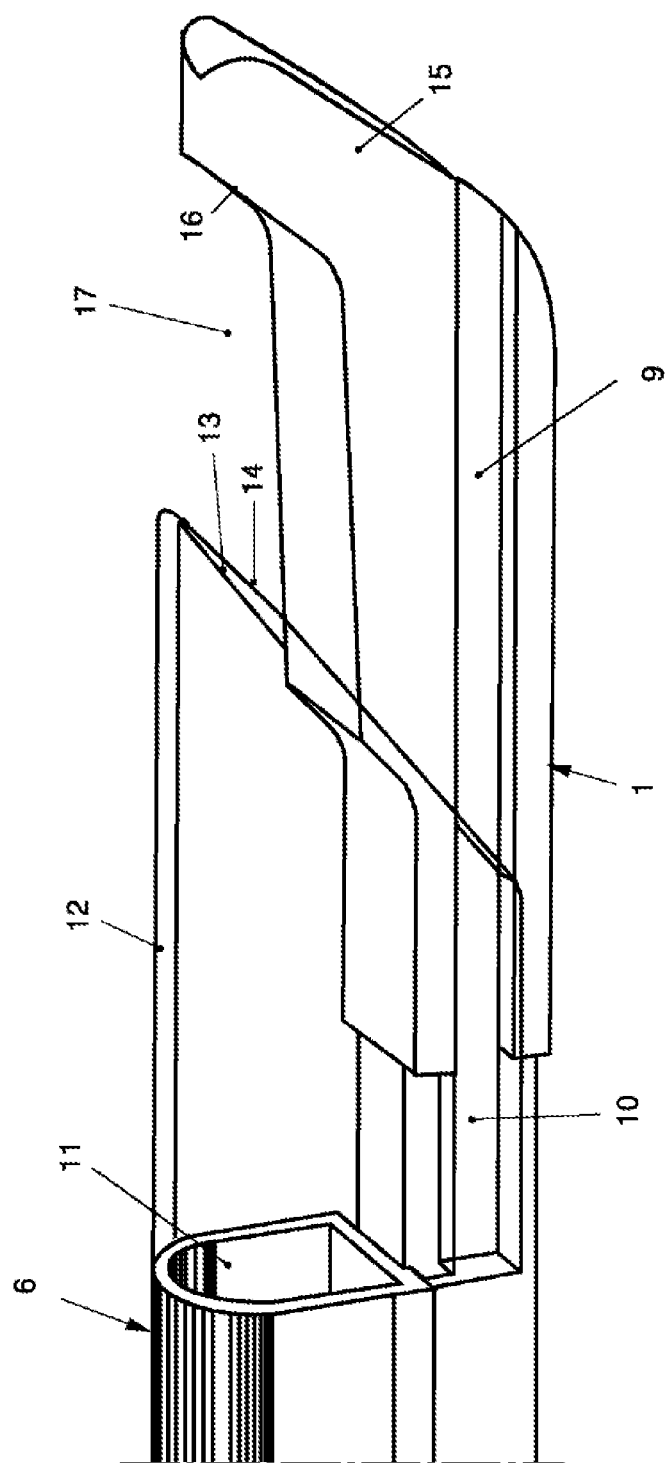
FIG. 4 shows a perspective view of the distal region of the device according to the invention from FIG. 1, wherein a subregion of a distal end of a slide rail is shown in transparent form.

According to the invention, the slide rail 6, as can be seen in particular in FIG. 4, is hollow and thus forms a suction channel 11. At the distal end of the slide rail 6, this suction channel 11 opens into a cutting piece 12 which forms a cutting opening 13. This cutting opening 13 is bounded by a cutting edge 14. The cutting opening 13 has a semi-oval configuration.

Since the cutting piece 12 is open at the bottom, it encloses a distal region of the guide rail 1 on both sides and there forms the abovementioned rails 10, which slide in the guide grooves 9 of the guide rail.

A mating cutting element 15 is formed, integrally in the present illustrative embodiment, on the distal end of the guide rail 1. Toward the cutting opening 13 of the slide rail 6, the mating cutting element 15 forms a semicircular cutting edge 16, which is adapted in terms of its contour to the cutting opening 13. Cutting opening 13 and mating cutting element 15 with the cutting edge 16 are configured such that the mating cutting element 15 can be received in the cutting opening 13 when the slide rail 6 is moved to the closed position, wherein the cutting or punching mouth 17 formed by the two cutting edges 14 and 16 closes.

Figure 2:
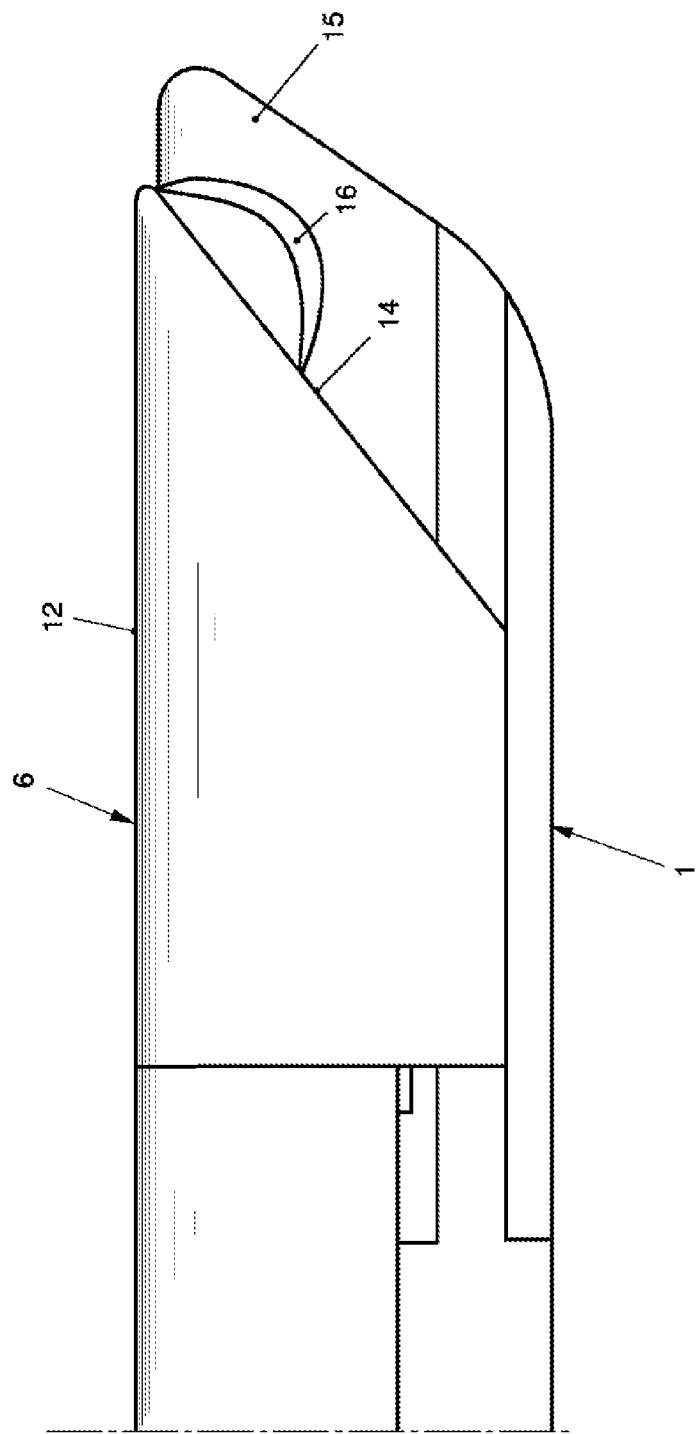
FIG. 2 shows an enlarged plan view of a distal end of the device according to the invention from FIG. 1, with a partially closed cutting or punching mouth.

As can be seen in particular in FIG. 2, the cutting edge 14 is set at an inclination to the cutting edge 16 such that, upon closure of the cutting or punching mouth 17, a scissors-like closure movement takes place between both cutting edges 14 and 16, by which the cutting action is substantially improved.

It is also indicated in FIG. 1 that a conduit 18 for supplying a liquid to the cutting or punching mouth 17 is located on the slide rail 6. This conduit 18 has an attachment to a liquid source (not shown in any detail).

Figure 3:
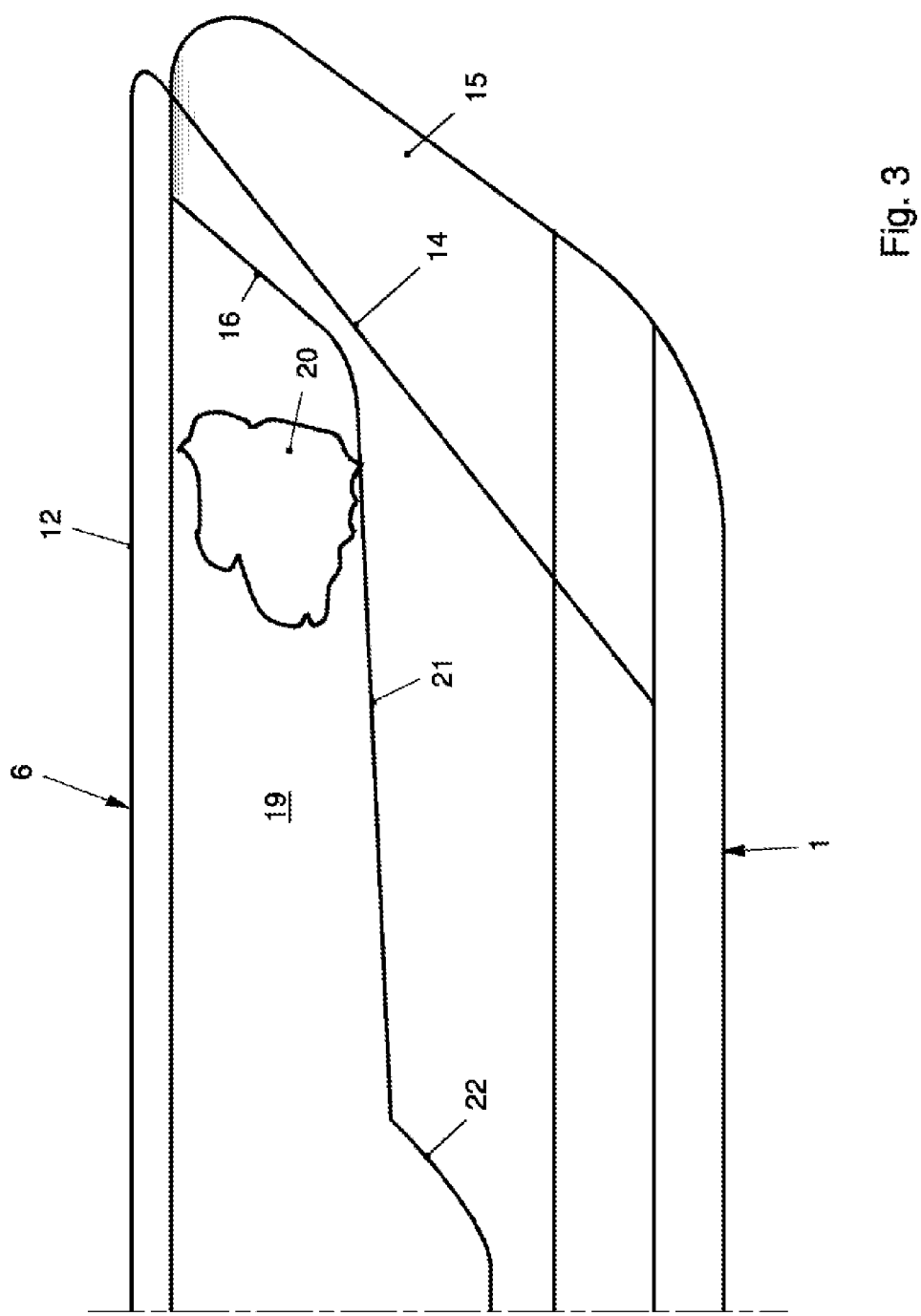
FIG. 3 shows an enlarged plan view of the distal region of the device according to the invention from FIG. 2, with a completely closed cutting or punching mouth.

The function of the present invention is as follows:

The device according to the invention can be inserted into the body of a human being, for example through a trocar or a suitably created opening in the body, in order to remove a tissue part 20 of any given kind. This tissue part 20 is brought into the region of the cutting or punching mouth 17, after which the cutting or punching mouth 17 is closed. The tissue is thus shorn off by the two cutting edges 14 and 16 and received in a cavity 19, shown in particular in FIG. 3. It can be seen that a bottom 21 of the cavity 19 is formed by the guide rail 1 and slopes gently down toward the rear, such that the cavity 19 opens rearwardly toward the suction channel 11. This makes the aspiration of the tissue part 20 easier. This is also made easier by a step 22 just before the suction channel 11. When the cutting piece 12 is moved rearward during the opening of the cutting or punching mouth, it already carries the tissue part 20 with it, such that the suction effect in the suction channel 11 is assisted.

The aspiration of the tissue part 20 is further assisted by the liquid supplied from the conduit 18. Particularly when the cutting or punching mouth 17 closes, the suction action in this region increases in the manner of a nozzle, such that a direct aspiration of the liquid is also effected through the cutting or punching mouth 17 directly into the suction channel 11, as a result of which a certain flushing of the suction channel 11 can be carried out, such that firmly stuck tissue parts 20 are also carried away. For this purpose, the conduit 18 preferably opens out shortly above the cutting opening 13.

The device P according to the invention, as shown in FIGS. 5 to 10, for severing and removing tissue parts not shown in any detail, in particular from a body of a living being, is likewise designed similarly to a known tissue punch. It has a guide rail (30) which, in this illustrative embodiment, is connected fixedly to a forceps grip. The further forceps grip (4) is connected to the forceps grip (2) via the rotary joint (3) and forms the articulated connection (5) with a slide rail (31). After the articulated connection (5), the slide rail (31) opens into the rotary valve (7), which transitions into the connector nipple (8), for example for attachment of a suction hose. A movement of the slide rail (31) with respect to the guide rail (30) is effected by a closing movement of the two forceps grips (2) and (4) relative to each other, wherein the slide rail (31) according to FIG. 10 has a groove (34) in which is guided a sliding block (35) protruding from the guide rail (30). The sliding block (35) is T-shaped. Corresponding to it, the groove (34) is configured as an undercut groove, wherein a front region (36) of this groove (34) is in turn configured such that the sliding block (35) can be inserted into the groove (34). For this purpose, the contour of the front region (36) corresponds approximately to the contour of the sliding block (35). This arrangement is known in bone punches.

The conduit (18) for supplying a liquid to a cutting or punching mouth (32) is located on the slide rail (31), wherein the conduit (18) likewise has a connector nipple (37) at the other end. The latter serves for attaching the conduit (18) to a liquid source (not shown in any detail).

A closure slide (38) is provided under the guide rail (30) and is indicated in FIG. 1 only by a small portion. It lies under the guide rail (30), as can be seen in part in FIG. 10, from a trigger slide (39) as far as the cutting and punching mouth, as is described later. The trigger slide (39) can be moved along the guide rail (30) and is preferably under spring pretensioning.

According to FIGS. 6 to 9, the cutting and punching mouth (32) is composed of a fixed part (40) which, for example, is integrally connected to the guide rail (30). It is configured like a trough and has a U-shaped border (41) which forms a U-shaped cutting edge (42) on the inside.

The fixed part (40) is assigned a movable cutting element (43), which is coupled to the guide rail (30) via a rotary joint (44).

The movement of the cutting element (43) about the rotary joint (44) is effected by displacement of the slide rail (31) in relation to the guide rail (30), wherein the slide rail (31) forms an articulated connection (45) with the cutting element (43).

A recess (46) is formed in the cutting element (43) and, when the cutting element (43) is opened, permits engagement of the conduit (18) or of its outlet opening (47), such that liquid from the conduit (18) can be introduced directly into the region of the cutting and punching mouth (32).

Figure 7:
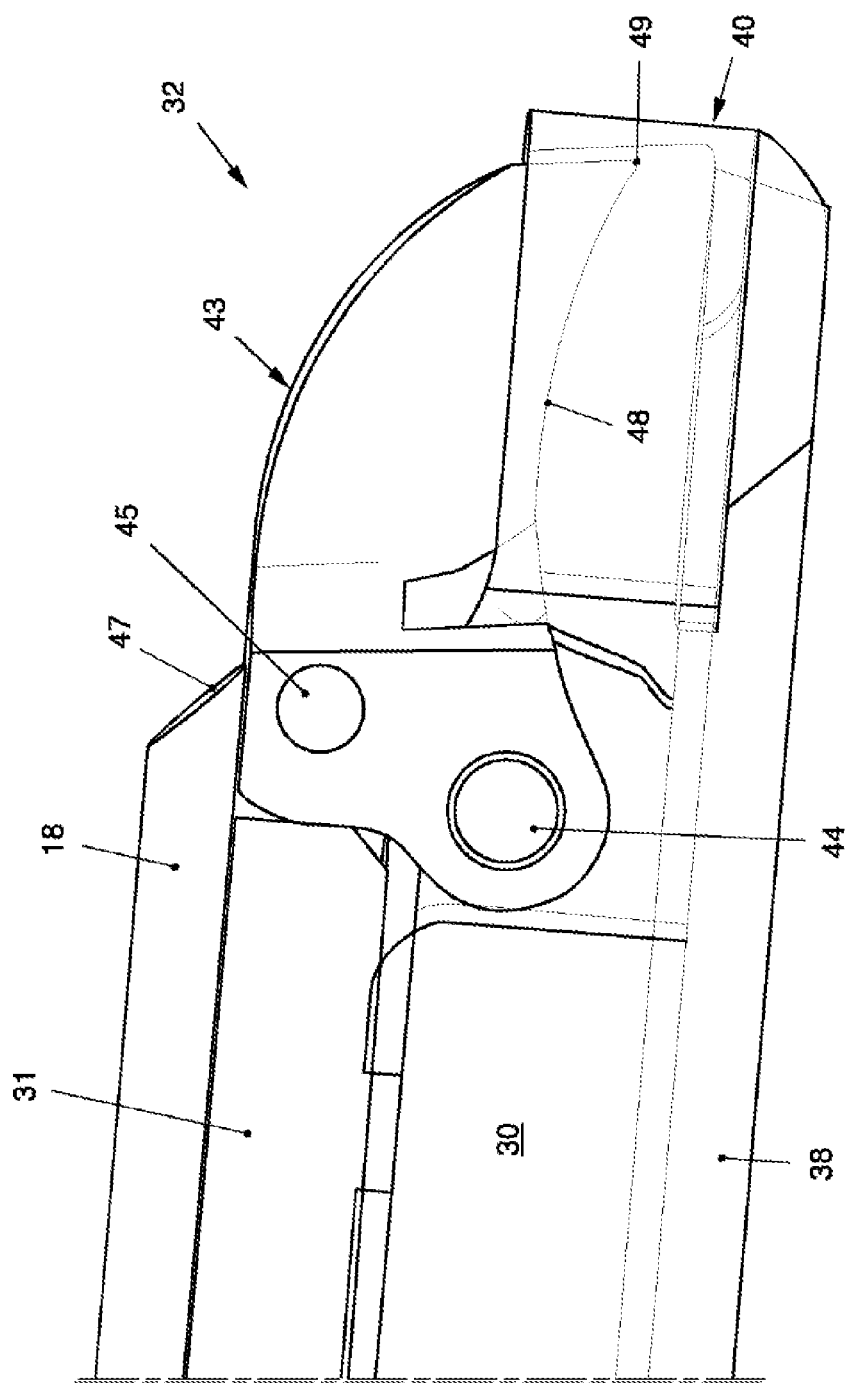
FIG. 7 shows an enlarged and partially transparent side view of the distal end of the device from FIG. 5.

It will be seen from FIG. 7 that the cutting element (43) forms a cutting edge (48) which on both sides extends concavely to a tip (49) of the cutting element (43). This is of particular advantage since the tip (49), together with the fixed part (40) of the cutting and punching mouth (32), grasps the most distant part of the tissue and/or buries its way into the tissue, and it is only then that the cutting action of the cutting edge (48) together with the cutting edge (42) takes place. By virtue of the concave configuration of the cutting edge (48), there is also no linear contact between cutting edge (42) and cutting edge (48) and instead only a punctiform contact as in scissors, as a result of which the ongoing cutting action is greatly facilitated and less force is needed for the cutting.

It will be seen from FIGS. 8 and 9 that the fixed part (40), that is to say the bottom (50) thereof, has an opening (51) extending through it. As will be seen in particular from FIG. 9, this opening (51) is bounded at least partially by a scraper element (52), wherein this scraper element (52) has an inner contour (53) which interacts with an outer contour (54) of the closure slide (38) such that the opening (51) can be closed by the closure slide (38) and the scraper element (52).

According to FIG. 8, the fixed part (40) of the cutting and punching mouth (32) is not integrally connected to the guide rail (30) but instead is part of a push-on element (55) which is pushed onto a cover strip (56) which in turn protrudes from the guide rail (30). The push-on element (55) engages over this cover strip (56) via two edge strips (57.1) and (57.2), such that a rail-shaped guide is obtained. The edge strips (57.1) and (57.2) each have a notch (58.1) and (58.2), into each of which a respective side tab (59.1) and (59.2) is inserted or bent. This configuration permits easy exchange of the push-on element (55), as a result of which the fixed part (40) of the cutting and punching mouth (32) can be replaced by another element.

Moreover, it can be clearly seen from FIG. 8 that the fixed part (40) forms a trough-shaped collecting space (60) for tissue parts or tissue fragments, which can then be aspirated through a suction channel (33) extending through the push-on element (55) and the guide rail (30).

The function of the present invention is as follows:

The device P1 according to the invention can be inserted into the body of a human being, for example through a trocar or a suitably created opening in the body, in order to remove a tissue part of any given kind. The tissue part is brought into the region of the cutting or punching mouth (32), after which this cutting or punching mouth (32) is closed. The tip (49) of the cutting element (43) digs into the tissue, and the tissue part is drawn into the collecting space (60). By further closure of the cutting element (43), the tissue part is shorn off by interaction with the cutting edge (42) of the fixed part (40).

At the same time, liquid is supplied through the conduit (18), wherein this liquid can also pass through the recess (46) into the collecting space (60) of the cutting and punching mouth (32). This liquid assists the aspiration of the severed tissue part through the suction channel (33). If the tissue part becomes stuck somewhere, it is additionally entrained by the liquid.

Figure 5:
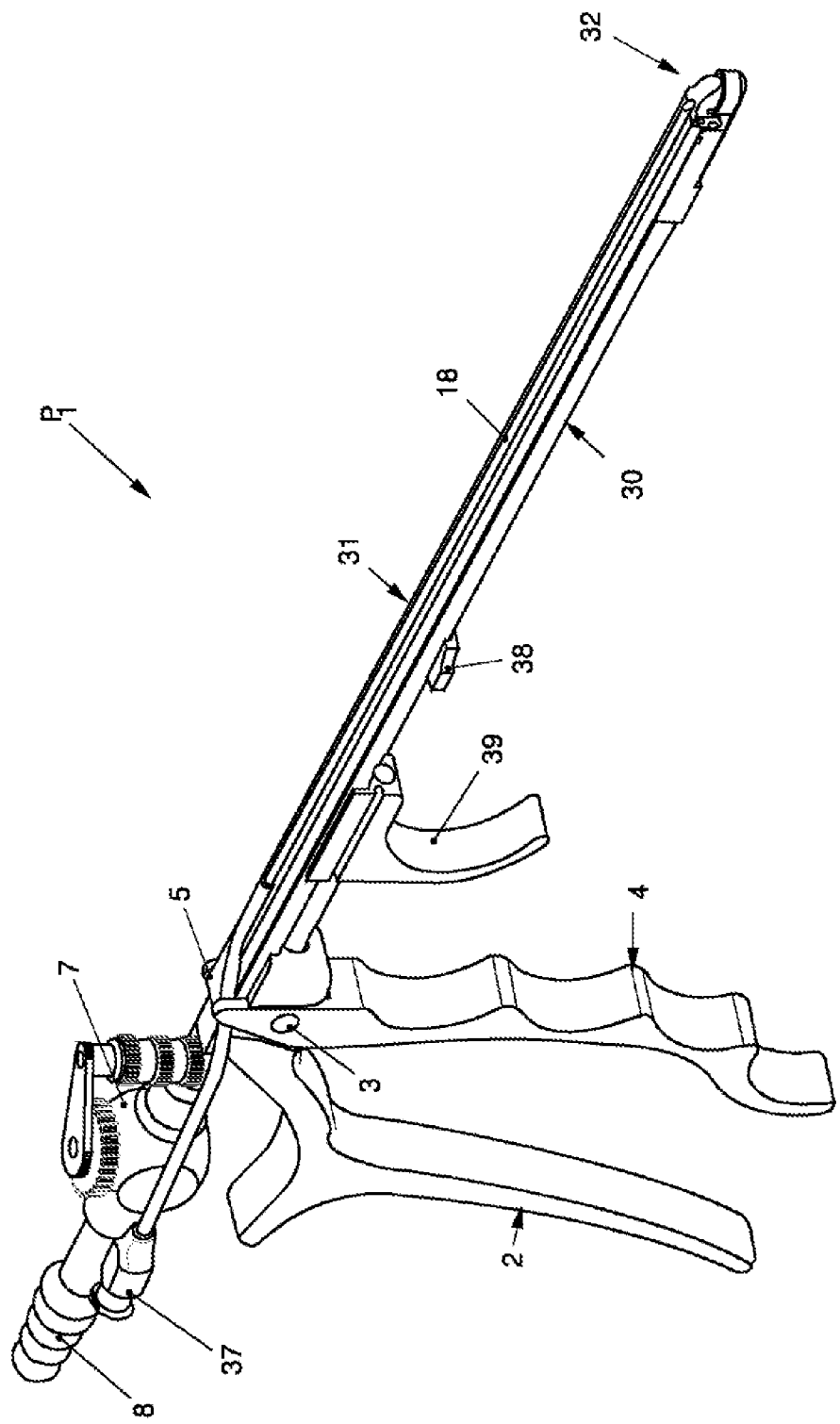
FIG. 5 shows a perspective view of a further illustrative embodiment of a device according to the invention for severing and removing tissue parts, with a closed cutting or punching mouth.
Figure 6:
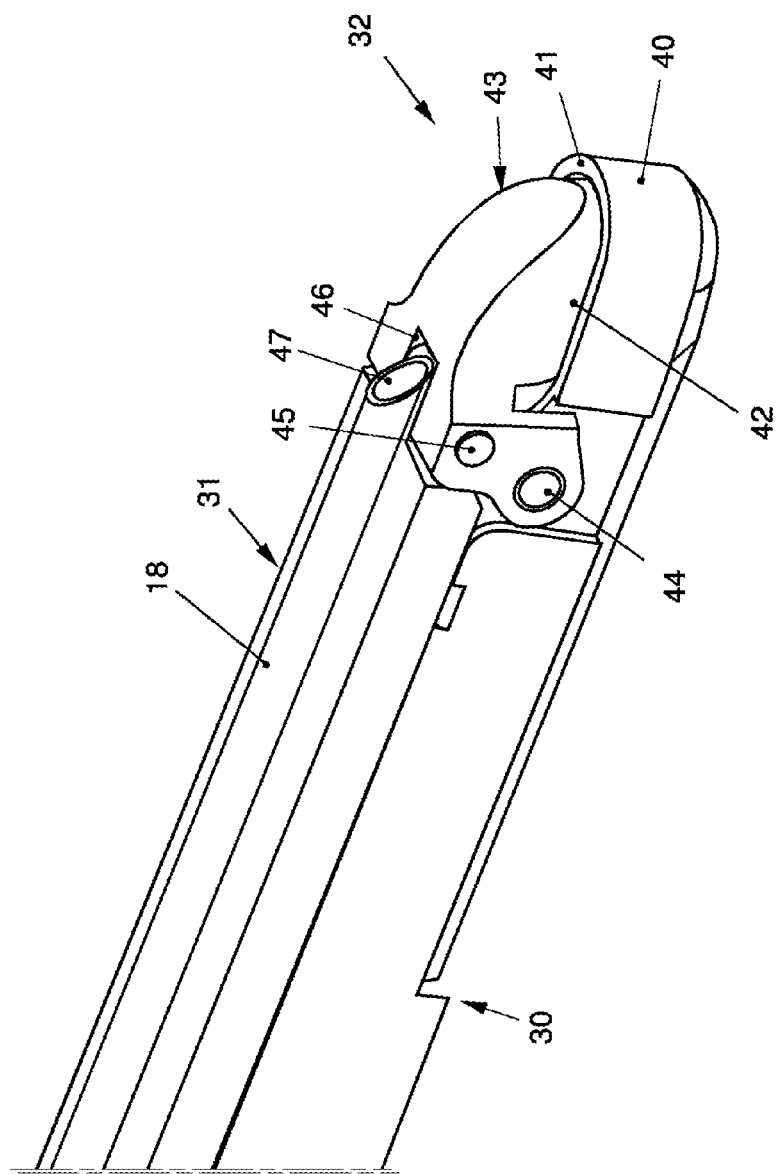
FIG. 6 shows an enlarged perspective view of the distal end of the device from FIG. 5.

Whereas the opening (51) in the bottom (50) of the fixed part (40) is closed during the described procedure, this opening (51) is opened for desired scraping of a tissue part or bone part, in which case the closure slide (38) is displaced by means of the trigger slide (39) to the proximal part of the device P1. The opening (51) is opened, as is shown in FIG. 5, wherein the closure slide (38) is in fact drawn back still farther so that the scraper element (52) can become operative. The scraper element (52) has a scraping edge (61) which is relatively sharp, such that a bone can be scraped off, for example.

The scraped-off tissue part can pass through the opening (51) into the collecting space (60) and is there aspirated through the suction channel (33), especially after the closure slide (38) has been moved forward toward the scraper element (52) by means of the trigger slide (39) and has closed the opening (52).

LIST OF REFERENCE NUMBERS 1 guide rail
2 forceps grip
3 rotary joint
4 forceps grip
5 articulated connection
6 slide rail
7 valve
8 connector nipple
9 guide groove
10 rail
11 suction channel
12 cutting piece
13 cutting opening
14 cutting edge
15 mating cutting element
16 cutting edge
17 cutting or punching mouth
18 conduit
19 cavity
20 tissue parts
21 bottom
22 step
30 guide rail
31 slide rail
32 scraping and punching mouth
33 suction channel
34 groove
35 sliding block
36 front region
37 connector nipple
38 closure slide
39 suction scraper
40 fixed part
41 border
42 cutting edge
43 cutting element
44 rotary joint
45 articulated connection
46 recess
47 outlet opening
48 cutting edge
49 tip
50 bottom
51 opening
52 scraper element/curette
53 inner contour
54 outer contour
55 push-on element
56 cover strip
57 edge strip
58 notch
59 side tab
60 collecting space
61 scraping edge
P device
P1 device

The invention claimed is:

1. A device for severing and removing tissue parts (20) from a body of a living being, comprising: a fixed guide rail (1, 30) and a slide rail (6, 31), wherein the slide rail is movable along the fixed guide rail, the slide rail (6, 31) at least partially forms a suction channel for removal of the severed tissue parts (20) and, in the distal region, the fixed guide rail and the slide rail define a cutting or punching mouth (17, 32) for severing the tissue parts (20), and wherein a conduit (18) for supplying a liquid is defined near the cutting or punching mouth (17) and outside of the suction channel (33), and wherein the conduit is mounted to an outside surface of at least one of the fixed guide rail (1, 30) and the slide rail (6, 31).

2. The device as claimed in claim 1, wherein the cutting or punching mouth (32) forms a lower, fixed part (40) through which an opening (51) at least partially extends, and wherein a scraping element/curette (52) is assigned to the opening (51).

3. The device as claimed in claim 2, wherein the opening (51) is closable.

4. The device as claimed in claim 3, wherein a closure slide (38) is assigned to the opening (51), and wherein the closure slide (38) is connected to a trigger slide (39).

5. The device as claimed in claim 1, wherein a cutting element (43) as part of the cutting or punching mouth (32) is arranged at the distal end of the slide rail (31), and wherein the cutting element (43) has, in the direction of an outlet opening (47) of the conduit (18), a passage (46) for the liquid.

6. The device as claimed in claim 5, wherein the cutting element (43) has a cutting edge (48) which interacts with the fixed part (40).

7. The device as claimed in claim 6, wherein the cutting edge (48) has a concave shape toward a tip (49).

8. The device as claimed in claim 7, wherein the cutting edge (48) has the concave shape toward the tip (49) on both sides.

9. The device as claimed in claim 6, wherein a cutting edge (48) which forms the fixed part (42) has a rectilinear shape.

10. The device as claimed in claim 1, wherein the conduit (18) opens out above a cutting edge (14) of a cutting opening (13) of the slide rail (6).

11. The device as claimed in claim 10, wherein a mating cutting element (15) protrudes at the distal end of the guide rail (9).

12. The device as claimed in claim 11, wherein the mating cutting element (15) forms a semicircular cutting edge (16).

13. The device as claimed in claim 11, wherein a cutting edge (14) of the cutting opening (13) of the slide rail (6) is set at an incline to the cutting edge (16) of the mating cutting element (15).

14. The device as claimed in claim 11, wherein the mating cutting element (15) is connected in one piece to the guide rail (1).

15. The device as claimed in claim 1, wherein the slide rail (6), at its distal end, forms a semi-oval cutting opening (13).

16. The device as claimed in claim 15, wherein the contour of the cutting opening (13) at the distal end of the slide rail (6) interacts with the contour of a semicircular cutting edge (16) at a mating cutting element (15), wherein the mating cutting element (15) travels into the cutting opening (13).

17. The device as claimed in claim 1, wherein the guide rail (1) forms a step (22) in the region of the cutting or punching mouth (17).

18. The device as claimed in claim 1, wherein the slide rail together with the guide rail forms the suction channel.

19. A device for severing and removing tissue parts (20) from a body of a living being, comprising: a fixed guide rail (1, 30) and a slide rail (6, 31), wherein the slide rail is movable along the fixed guide rail, and the fixed guide rail (1, 30) and the slide rail (6, 31) form, in the distal region, a cutting or punching mouth (17, 32) for severing the tissue parts (20),
wherein the cutting or punching mouth (17, 32) is defined by spaced cutting edges (14, 16) which are angled relative to each other such that a distance between the spaced cutting edges (14, 16) decreases distally, and wherein a conduit (18) for supplying a liquid is defined near the cutting or punching mouth (17), wherein the fixed guide rail (1, 30) has a first cutting edge (16) of the spaced cutting edges that protrudes upwardly at the distal end of the fixed guide rail, and
wherein during movement of the slide rail along the fixed guide rail, the distal end of the slide rail defining a second cutting edge (14) of the cutting edges is guided over the first cutting edge (16) of the fixed guide rail, wherein the spaced cutting edges interact like scissors, wherein both of the spaced cutting edges (14, 16) are inclined from vertical, and wherein the second cutting edge (14) of the spaced cutting edges is inclined more from the vertical than the first cutting edge (16).

20. The device as claimed in claim 19, wherein a second cutting edge of the spaced cutting edges is defined on the distal end of the slide rail such that, during movement of the slide rail along the fixed guide rail, the first cutting edge and the second cutting edge interact like scissors.

* * * * *